(12) United States Patent
Wang et al.

(10) Patent No.: US 10,983,099 B2
(45) Date of Patent: Apr. 20, 2021

(54) METHOD FOR QUANTITATIVE DETECTION OF TRACE POLYLACTIC ACID MICROPLASTICS IN ENVIRONMENTAL SAMPLE

(71) Applicant: Nankai University, Tianjin (CN)

(72) Inventors: Lei Wang, Tianjin (CN); Yali Xu, Tianjin (CN); Xuejiao Tang, Tianjin (CN); Chu Peng, Tianjin (CN); Hongwen Sun, Tianjin (CN)

(73) Assignee: Nankai University, Tianjin (CN)

( * ) Notice: Subject to any disclaimer, the term of this patent is extended or adjusted under 35 U.S.C. 154(b) by 0 days.

(21) Appl. No.: 16/865,831

(22) Filed: May 4, 2020

(65) Prior Publication Data

US 2021/0072202 A1   Mar. 11, 2021

(30) Foreign Application Priority Data

Sep. 11, 2019   (CN) .......................... 201910861095.9

(51) Int. Cl.
*H01J 49/04* (2006.01)
*G01N 30/72* (2006.01)
*G01N 30/02* (2006.01)

(52) U.S. Cl.
CPC ...... *G01N 30/7233* (2013.01); *H01J 49/0431* (2013.01); *G01N 2030/027* (2013.01)

(58) Field of Classification Search
CPC .......... G01N 30/7233; G01N 2030/027; H01J 49/0431
See application file for complete search history.

(56) References Cited

U.S. PATENT DOCUMENTS

| | | | | |
|---|---|---|---|---|
| 5,618,911 A * | 4/1997 | Kimura | .................. | C08G 63/08 525/354 |
| 5,728,847 A * | 3/1998 | Ohara | .................. | C07D 319/12 549/274 |
| 2002/0132967 A1* | 9/2002 | Ohara | .................. | C07D 319/12 528/354 |
| 2010/0174004 A1* | 7/2010 | Wu | ...................... | C08L 23/0853 521/84.1 |
| 2013/0096342 A1* | 4/2013 | Srinivasan | ............ | C07C 51/412 562/589 |
| 2015/0290840 A1* | 10/2015 | Boisart | ...................... | C12P 7/44 435/139 |
| 2017/0349613 A1* | 12/2017 | Cantat | .................... | C07F 7/1804 |
| 2018/0051156 A1* | 2/2018 | Foley | .................... | B01J 13/0065 |
| 2019/0218360 A1* | 7/2019 | Desrousseaux | .......... | C08J 11/14 |
| 2019/0345472 A1* | 11/2019 | Marty | .................... | C12N 15/52 |

* cited by examiner

*Primary Examiner* — David J Bolduc
(74) *Attorney, Agent, or Firm* — Howard & Howard Attorneys PLLC

(57) ABSTRACT

A method for quantitative detection of trace polylactic acid microplastics (PLA MPs) in an environmental sample is disclosed, where the PLA MP in the environmental sample is depolymerized in an alkaline alcohol phase system, and the monomers thereof, i.e., lactic acid molecules were separated and recovered. Mass concentrations of lactic acid before and after reaction are quantitatively detected by HPLC-MS, and the initial mass concentration of PLA MPs in the sample is calculated using a formula. The minimum detectable concentration may be as low as 0.05 mg/kg. This method can quantify the trace PLA in water body, sludge, sediment, dust, and soil samples; no special treatment is required before heating in pentanol; use of such reaction conditions as heating and alkaline alcohol phase reduces reaction time substantially.

7 Claims, No Drawings

METHOD FOR QUANTITATIVE DETECTION OF TRACE POLYLACTIC ACID MICROPLASTICS IN ENVIRONMENTAL SAMPLE

CROSS-REFERENCE TO RELATED APPLICATION(S)

The present application claims priority to and the benefit of Chinese Patent Application Serial No. 201910861095.9, filed Sep. 11, 2019, the entire disclosure of which is hereby expressly incorporated by reference.

TECHNICAL FIELD

The present invention relates to the technical field of environmental monitoring, and in particular to a method for quantitative detection of trace polylactic acid microplastics (PLA MPs) in environmental samples, e.g., water body, sludge, sediment, dust, and soil.

BACKGROUND

With the increasing use of plastic products, microplastics (MPs) are inevitably present in the environment. Due to slow degradation, the majority of MPs will accumulate in the environment constantly, aggravating the pollution increasingly. Therefore, MPs, as a novel type of environmental pollutant, have attracted wider attention. A problem is that nondegradable plastics, e.g., polyethylene (PE) and polypropylene (PP), are refractory in the environment. In view of this, degradable plastics, represented by polylactic acid (PLA), will be one of the development directions of plastics industry and one of the solutions to the abatement of current nondegradable plastic pollution. PLA, also known as polylactide, is a polyester polymerized with lactic acid as a raw material; compared with conventional plastics, PLA can be degraded to $CO_2$ and $H_2O$ by microbes and light in natural environments. Waste PLA plastics will enter the environment inevitably and be degraded to MPs, but concentrations of PLA plastics have not been detected quantitatively in different environmental samples. At present, to establish an accurate and efficient microplastics assay is a foundation for research on microplastics environment. In the existing microplastics assay, microplastic particles are mainly screened out by means of flotation and digestion, followed by qualitative analysis by infrared spectrometry and Raman spectrometry, and by visual quantification under microscopy. This will lead to a difficult literature-literature comparison, and subjective judgments by operators may also cause bigger errors. Therefore, it is necessary to develop a method for quantitative detection of trace PLA MPs in different environmental samples.

SUMMARY

To overcome the defects in the prior art, the present invention proposes a method for quantitative detection of trace polylactic acid microplastics (PLA MPs) in an environmental sample, where direct alkali-catalyzed thermal depolymerization of the environmental sample in an alkaline pentanol system allows the trace PLA in the environmental sample to depolymerize into lactic acid monomers, concentrations of functional lactic acid monomer in the system before and after depolymerization are quantitatively detected by HPLC-MS, and a concentration of PLA in the environmental sample is backtracked using a formula, including the following steps of:

1) charging the environmental sample and potassium hydroxide into a 100 mL round-bottom flask, adding n-pentanol, and conducting thermal depolymerization;

2) after cooling down the reaction mixture in step (1) naturally, adding 20 mL of ultrapure water and subsequently transferring to a 50 mL centrifuge tube; after oscillation and centrifugation, isolating an upper-layer pentanol extract and transferring to another 50 mL centrifuge tube, adding 20 mL of ultrapure water, and repeating the preceding extraction (oscillation, centrifugation, and isolation) process; combining the above two lower-layer aqueous phases obtained, and diluting to 50 mL with ultrapure water; adjusting pH to 6 to 8 with hydrochloric acid, pipetting 10 mL therefrom, and extracting lactic acid monomers with MAX SPE cartridges;

3) using HPLC-MS to detect a concentration of the lactic acid recovered in step 2), and detecting a concentration of background lactic acid in the environmental sample dissolved in 10 mL of methanol; and 4) using a formula to calculate an initial concentration of PLA in the environmental sample.

The environmental sample includes suspended particles of water body, sludge, sediment, dust, or soil sample.

A minimum detectable concentration of the trace PLA may be as low as 0.05 mg/kg.

The environmental sample requires no special treatment before heating in pentanol.

The thermal depolymerization time is 10 to 30 min.

The depolymerizing temperature is 120 to 150° C.

The calculation formula is:

$$W_{PLA} = \frac{(W_{Lactic\ acid\ 1} \times V_1 - W_{Lactic\ acid\ 0} \times V_0) \times M_1}{M_2 \times m_0}$$

where: $W_{PLA}$ is a mass concentration of PLA in the environmental sample, in mg/kg;

$W_{Lactic\ acid\ 1}$ and $W_{Lactic\ acid\ 0}$ are concentrations of lactic acid in the system after and before depolymerization, respectively, in mg/L;

$M_1$ and $M_2$ are molar masses of structural unit of PLA polymer and lactic acid monomer, respectively, in g/mol;

$V_1$ and $V_0$ are volumes of liquid phase reaction system after and before depolymerization, respectively, in L; and $m_0$ is sample mass, in kg.

Compared with the prior art, the present invention has the following advantages and positive effects: the method is universally applicable to suspended particles of water body, sludge, sediment, dust, and soil samples, and features wide application and ability to quantitatively detect trace PLA MPs in environmental samples, with a minimum detectable concentration of as low as 0.05 mg/kg; no special treatment is required before heating in pentanol; use of such reaction conditions as heating and alkaline alcohol phase reduces reaction time substantially, and ensures a depolymerization rate of >99% and accurate quantification.

DETAILED DESCRIPTION

The present invention will be described below further in combination with embodiments, but they should not be construed as limiting the scope of the invention. It should be merely noted herein that both kits and test equipment used in the present invention are commercially available, unless specified otherwise.

Embodiment 1

A method for quantitative detection of trace PLA MPs in an environmental sample was described. Direct alkali-catalyzed thermal depolymerization of the environmental sample in an alkaline pentanol system allowed the trace PLA in the environmental sample to depolymerize into lactic acid monomers, concentrations of functional lactic acid monomer in the system before and after depolymerization were quantitatively detected by HPLC-MS, and a concentration of PLA in the environmental sample was backtracked using a formula, including the following steps of:

1) charging 0.1 g of soil sample and 0.5 g of potassium hydroxide into a 100 mL round-bottom flask, adding 20 ml of n-pentanol, and conducting thermal depolymerization for 20 min at 135° C.;

2) after cooling down the reaction mixture in step (1) naturally, adding 20 mL of ultrapure water and subsequently transferring to a 50 mL centrifuge tube; after oscillation and centrifugation, isolating an upper-layer pentanol extract and transferring to another 50 mL centrifuge tube, adding 20 mL of ultrapure water, and repeating the preceding extraction (oscillation, centrifugation, and isolation) process; combining the above two lower-layer aqueous phases obtained, and diluting to 50 mL with ultrapure water; adjusting pH to 6 to 8 with hydrochloric acid, pipetting 10 mL therefrom, and extracting lactic acid monomers with MAX SPE cartridges;

3) using HPLC-MS to detect a concentration of the lactic acid monomer recovered in step 2), and detecting an initial concentration of the lactic acid in 0.1 g of the soil sample dissolved in 10 mL of methanol; and 4) using a formula to calculate an initial concentration of PLA in the soil sample, i.e., 1.7 mg/kg.

Embodiment 2

A method for quantitative detection of trace PLA MPs in an environmental sample was described. Direct alkali-catalyzed thermal depolymerization of the environmental sample in an alkaline pentanol system allowed the trace PLA in the environmental sample to depolymerize into lactic acid monomers, concentrations of functional lactic acid monomer in the system before and after depolymerization were quantitatively detected by HPLC-MS, and a concentration of PLA in the environmental sample was backtracked using a formula, including the following steps of:

1) charging 0.1 g of lake sediment sample and 0.5 g of potassium hydroxide into a 100 mL round-bottom flask, adding 20 ml of n-pentanol, and conducting thermal depolymerization for 30 min at 130° C.;

2) after cooling down the reaction mixture in step (1) naturally, adding 20 mL of ultrapure water and subsequently transferring to a 50 mL centrifuge tube; after oscillation and centrifugation, isolating an upper-layer pentanol extract and transferring to another 50 mL centrifuge tube, adding 20 mL of ultrapure water, and repeating the preceding extraction (oscillation, centrifugation, and isolation) process; combining the above two lower-layer aqueous phases obtained, and diluting to 50 mL with ultrapure water; adjusting pH to 6 to 8 with hydrochloric acid, pipetting 10 mL therefrom, and extracting lactic acid monomers with MAX SPE cartridges;

3) using HPLC-MS to detect a concentration of the lactic acid monomer recovered in step 2), and detecting an initial concentration of the lactic acid in 0.1 g of the sediment sample dissolved in 10 mL of methanol; and 4) using a formula to calculate an initial concentration of PLA in the sediment sample, i.e., 2.1 mg/kg.

The present invention discloses a method for quantitative detection of trace PLA MPs in an environmental sample, and may be achieved by alteration of such links as process route by those skilled in the art on the basis of the present invention. Although the invention has now been described with reference to the preferred embodiments, modifications or recombinations in the method of the invention will be apparent to those skilled in the art without departing from the scope and the spirit of the invention. It should be particularly noted that all similar substitutions or alterations will be evident to those skilled in the art and will be construed as being included in the spirit and the scope of the present invention.

What is claimed is:

1. A method for quantitative detection of trace polylactic acid microplastics (PLA MPs) in an environmental sample, wherein direct alkali-catalyzed thermal depolymerization of the environmental sample in an alkaline pentanol system allows the trace PLA component in the environmental sample to depolymerize into lactic acid monomers, concentrations of functional lactic acid monomer in the system before and after depolymerization are quantitatively detected by HPLC-MS, and a concentration of PLA in the environmental sample is backtracked using a formula, comprising the following steps of:

1) charging the environmental sample and potassium hydroxide into a 100 mL round-bottom flask, adding n-pentanol, and conducting thermal depolymerization;

2) after cooling down the reaction mixture in step (1) naturally, adding 20 mL of ultrapure water and subsequently transferring to a 50 mL centrifuge tube; after oscillation and centrifugation, observing a phase separation of an upper-layer pentanol phase and a lower-layer aqueous phase; isolating an upper-layer pentanol extract and transferring the upper-layer pentanol extract to another 50 mL centrifuge tube, adding 20 mL of ultrapure water, and repeating the preceding extraction (oscillation, centrifugation, and isolation) process; combining two lower-layer aqueous phases obtained after twice centrifugation, and diluting to 50 mL with ultrapure water; adjusting pH to 6 to 8 with hydrochloric acid, pipetting 10 mL therefrom, and extracting lactic acid monomers with MAX SPE cartridges;

3) using HPLC-MS to detect a concentration of the lactic acid recovered in step 2), and detecting a concentration of background lactic acid in the environmental sample dissolved in 10 mL of methanol; and 4) using a formula to calculate an initial concentration of PLA in the environmental sample.

2. The method for quantitative detection of trace PLA MPs in an environmental sample according to claim 1, wherein the environmental sample comprises sludge, sediment, dust, or soil sample.

3. The method for quantitative detection of trace PLA MPs in an environmental sample according to claim 1, wherein a minimum detectable concentration of the trace PLA is 0.05 mg/kg.

4. The method for quantitative detection of trace PLA MPs in an environmental sample according to claim 1, wherein the environmental sample is allowed for direct alkali-catalyzed thermal depolymerization in pentanol.

5. The method for quantitative detection of trace PLA MPs in an environmental sample according to claim 1, wherein the thermal depolymerization time is 10 to 30 min.

6. The method for quantitative detection of trace PLA MPs in an environmental sample according to claim 1, wherein depolymerizing temperature is 120 to 150° C.

7. The method for quantitative detection of trace PLA MPs in an environmental sample according to claim 1, wherein the calculation formula is:

$$W_{PLA} = \frac{(W_{Lactic\ acid\ 1} \times V_1 - W_{Lactic\ acid\ 0} \times V_0) \times M_1}{M_2 \times m_0}$$

wherein: $W_{PLA}$ is a mass concentration of PLA in the environmental sample, in mg/kg;

$W_{Lactic\ acid\ 1}$ and $W_{Lactic\ acid\ 0}$ are concentrations of lactic acid in the system after and before depolymerization, respectively, in mg/L;

$M_1$ and $M_2$ are molar masses of structural unit of PLA polymer and lactic acid monomer, respectively, in g/mol;

$V_1$ and $V_0$ are volumes of liquid phase reaction system after and before depolymerization, respectively, in L; and $m_0$ is sample mass, in kg.

* * * * *